US012752037B2

(12) United States Patent
Dickinson et al.

(10) Patent No.: US 12,752,037 B2
(45) Date of Patent: Oct. 6, 2026

(54) SPONGE ASSEMBLY

(71) Applicant: CFields, LLC, Virginia Beach, VA (US)

(72) Inventors: Anna Marie Dickinson, Virginia Beach, VA (US); Luke Weston Leidy, Virginia Beach, VA (US); William Andrew Dickinson, III, Virginia Beach, VA (US); Christopher Michael Sciortino, Virginia Beach, VA (US); Jella An, Bethesda, MD (US)

(73) Assignee: CFields, LLC, Virginia Beach, VA (US)

( * ) Notice: Subject to any disclaimer, the term of this patent is extended or adjusted under 35 U.S.C. 154(b) by 226 days.

(21) Appl. No.: 18/796,711

(22) Filed: Aug. 7, 2024

(65) Prior Publication Data

US 2025/0049983 A1 Feb. 13, 2025

Related U.S. Application Data

(60) Provisional application No. 63/531,183, filed on Aug. 7, 2023.

(51) Int. Cl.
*A61L 15/38* (2006.01)
*A61L 15/42* (2006.01)

(52) U.S. Cl.
CPC ............ *A61L 15/425* (2013.01); *A61L 15/38* (2013.01); *A61L 2300/254* (2013.01)

(58) Field of Classification Search
CPC ... A61L 15/425; A61L 15/38; A61L 2300/254
See application file for complete search history.

(56) References Cited

U.S. PATENT DOCUMENTS 3,324,855 A 6/1967 Heimlich
4,875,602 A * 10/1989 Chickering ......... A61M 35/006
222/187

(Continued)

FOREIGN PATENT DOCUMENTS

WO WO2014035862 3/2014
WO WO2015175250 11/2015

OTHER PUBLICATIONS https://www.henryschein.com/assets/Medical/1245120.pdf.
(Continued)

*Primary Examiner* — Guy K Townsend
(74) *Attorney, Agent, or Firm* — Shaddock Law Group, PC

(57) ABSTRACT

A sponge assembly including at least some of a pipette having a pipette bulb portion including a hollow interior bulb portion and an elongate pipette body portion including a hollow interior body portion, wherein the pipette extends from the pipette bulb portion to the pipette body portion, wherein the pipette body portion extends from the pipette bulb portion to an open terminal end having an aperture, wherein the aperture of the pipette terminal end allows fluid communication between the open pipette terminal end, the hollow interior body portion, and the hollow interior bulb portion; a sponge support defining an at least partial cavity, wherein the open pipette terminal end is in fluid communication with the sponge support cavity, via the pipette aperture; and at least one sponge portion attached or coupled to the sponge support to cover at least a portion of the at least partial cavity.

20 Claims, 6 Drawing Sheets

(56) References Cited

U.S. PATENT DOCUMENTS

| | | | | | |
|---|---|---|---|---|---|
| 5,152,742 | A * | 10/1992 | Simpson | A45D 34/042 604/3 |
| 5,445,462 | A * | 8/1995 | Johnson | A61M 35/006 401/133 |
| 7,219,816 | B1 * | 5/2007 | Xia | A61J 1/067 222/215 |
| 7,232,310 | B2 * | 6/2007 | Han | A46B 11/0041 433/80 |
| 7,462,165 | B2 | 12/2008 | Ding et al. | |
| 11,317,933 | B1 * | 5/2022 | White | A61M 31/00 |
| 11,690,433 | B2 * | 7/2023 | Alicea-GarcÍA | A45D 29/17 132/73.5 |
| 2001/0055511 | A1 * | 12/2001 | Baumann | B65D 35/36 401/266 |
| 2005/0171467 | A1 | 8/2005 | Landman | |
| 2017/0266046 | A1 | 9/2017 | Steen et al. | |
| 2019/0388589 | A1 * | 12/2019 | Macphee | C12Y 203/02013 |

OTHER PUBLICATIONS https://www.anscare.com/en/product/detail/PVA_Eye_Spear.
https://www.bvimedical.com/products/fluid-control/.
https://pubmed.ncbi.nlm.nih.gov/16525952/.
https://fabco.net/catalog/ivalon/lasik-eye-sponge/.
https://optohellas.com/product/ophthalmology/iols-consumables/surgical-sponges/.
https://www.sdpmedical.com/en/ophthalmic-eye-spears.
https://tecfenmedical.com/pva-cellulose-eye-sponges/.

* cited by examiner

SPONGE ASSEMBLY

CROSS-REFERENCE TO RELATED APPLICATIONS

This patent application claims the benefit of U.S. Patent Application No. 63/531,183, filed Aug. 7, 2023, the disclosure of which is incorporated herein in its entirety by reference.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISC APPENDIX

Not Applicable.

NOTICE OF COPYRIGHTED MATERIAL

The disclosure of this patent document contains material that is subject to copyright protection. The copyright owner has no objection to the reproduction by anyone of the patent document or the patent disclosure, as it appears in the Patent and Trademark Office patent file or records, but otherwise reserves all copyright rights whatsoever. Unless otherwise noted, all trademarks and service marks identified herein are owned by the applicant.

BACKGROUND OF THE PRESENT DISCLOSURE

1. Field of the Present Disclosure

The present disclosure relates generally to the field of medical sponges.

2. Description of Related Art

It is generally known for surgeons to use sponges to manage blood removal during surgical procedures. For example, surgeons use eye spear sponges to manage blood removal during delicate eye surgery procedures. Typically, these products are made from cellulose or PVA for lint-free, high absorbency while maintaining rigidity during the wicking process.

Any discussion of documents, acts, materials, devices, articles, or the like, which has been included in the present specification is not to be taken as an admission that any or all of these matters form part of the prior art base or were common general knowledge in the field relevant to the present disclosure as it existed before the priority date of each claim of this application.

BRIEF SUMMARY OF THE PRESENT DISCLOSURE

Unfortunately, known tools and techniques have a number of shortcomings. For example, currently known sponges can easily become fully saturated, requiring the use of a large number of sponges during a given surgical procedure.

In order to overcome these and other shortcomings of known surgical sponges and sponge assemblies, the sponge assembly of the present disclosure provides a surgical sponge assembly for improved blood removal during a surgical procedure. In various exemplary, nonlimiting embodiments, the sponge assembly of the present disclosure also provides a clotting factor for longer visibility during surgeries.

In various exemplary embodiments, the sponge assembly is utilized as an eye sponge with diluted topical hemostatic agents supported by a microcapillary pipet. The sponge assembly may be utilized as a hemostatic and wicking aid for detailed, microscopic surgical procedures.

The sponge assembly of the present disclosure optionally includes an eye sponge with diluted hemostatic agents supported by a microcapillary pipette. The sponge assembly of the present disclosure serves as a hemostatic and wicking aid for detailed, microscopic surgical procedures.

In certain exemplary, nonlimiting embodiments, the sponge assembly of the present disclosure provides at least some of a pipette wherein the pipette includes a pipette bulb portion having a hollow interior bulb portion and an elongate pipette body portion having a hollow interior body portion, wherein the pipette extends from the pipette bulb portion to the pipette body portion, wherein the pipette body portion extends from the pipette bulb portion to a pipette terminal end, and wherein the pipette terminal end includes an aperture, which allows fluid communication between the open pipette terminal end, the hollow interior body portion, and the hollow interior bulb portion; a sponge support defining an at least partial cavity, wherein a pipette aperture is formed through a portion of the sponge support, and wherein at least a portion of the open pipette terminal end is in fluid communication with the pipette aperture, such that the open pipette terminal end is in fluid communication with the sponge support cavity, via the pipette aperture; and at least one sponge portion, wherein the at least one sponge portion is attached or coupled to the sponge support to cover at least a portion of the at least partial cavity.

In certain exemplary, nonlimiting embodiments, the pipette comprises a microcapillary pipette.

In certain exemplary, nonlimiting embodiments, a thrombin fluid or hemostatic agent is supplied within the hollow interior bulb portion or the hollow interior body portion.

In certain exemplary, nonlimiting embodiments, the at least one sponge portion is at least partially impregnated with a thrombin fluid or hemostatic agent.

In certain exemplary, nonlimiting embodiments, the pipette and the sponge support are formed as a single, integral unit.

In certain exemplary, nonlimiting embodiments, the sponge support is substantially triangularly shaped.

In certain exemplary, nonlimiting embodiments, the sponge support forms a substantially right triangle, wherein the sponge support bottom wall forms a base leg, the sponge support rear wall forms a height leg, and the upper edge portion of the sponge support sidewall forms a hypotenuse of the sponge support.

In certain exemplary, nonlimiting embodiments, the sponge support is formed of one or more walls.

In certain exemplary, nonlimiting embodiments, the sponge support includes a sponge support bottom wall, a sponge support side wall, and a sponge support rear wall.

In certain exemplary, nonlimiting embodiments, the at least one sponge portion comprises a first sponge portion and a second sponge portion.

In certain exemplary, nonlimiting embodiments, the sponge assembly of the present disclosure provides at least some of a pipette having a pipette bulb portion including a hollow interior bulb portion and an elongate pipette body portion including a hollow interior body portion, wherein the pipette extends from the pipette bulb portion to the pipette body portion, wherein the pipette body portion extends from the pipette bulb portion to an open terminal end having an aperture, wherein the aperture of the pipette terminal end allows fluid communication between the open pipette terminal end, the hollow interior body portion, and the hollow interior bulb portion; a sponge support defining an at least partial cavity, wherein a pipette aperture is formed through a portion of the sponge support, and wherein at least a portion of the open pipette terminal end is in fluid communication with the pipette aperture, such that the open pipette terminal end is in fluid communication with the sponge support cavity, via the pipette aperture; and at least one sponge portion, wherein the at least one sponge portion is attached or coupled to the sponge support to cover at least a portion of the at least partial cavity.

In certain exemplary, nonlimiting embodiments, the sponge assembly of the present disclosure provides at least some of a pipette having a pipette bulb portion and an elongate pipette body portion, wherein the pipette body portion extends from the pipette bulb portion to a pipette terminal end, and wherein the pipette terminal end includes an aperture, which allows fluid communication between the open pipette terminal end, a hollow interior body portion of the elongate pipette body portion, and a hollow interior bulb portion of the pipette bulb portion; a sponge support defining an at least partial cavity, wherein a pipette aperture is formed through a portion of the sponge support, and wherein at least a portion of the open pipette terminal end is in fluid communication with the pipette aperture, such that the open pipette terminal end is in fluid communication with the sponge support cavity, via the pipette aperture; and at least one sponge portion, wherein the at least one sponge portion is attached or coupled to the sponge support to cover at least a portion of the at least partial cavity.

The present disclosure separately and optionally provides a sponge assembly that utilizes a micropipette for easier and quicker clearance of blood or other fluid from a surgical field.

The present disclosure separately and optionally provides a sponge assembly that includes a sponge portion impregnated with or including a hemostatic agent.

The present disclosure separately and optionally provides a sponge assembly that includes a sponge portion having a thrombin or other hemostatic coating.

The present disclosure separately and optionally provides a sponge assembly that uses clotting factors coated on the sponge for longer-lasting visibility during surgeries.

The present disclosure separately and optionally provides a sponge assembly that may be utilized in various types of incisional surgery that require a high level of precision, such as ophthalmic surgeries, neurosurgeries, and plastic surgeries.

The present disclosure separately and optionally provides a sponge assembly that reduces disposables.

The present disclosure separately and optionally provides a sponge assembly that clears blood or other fluid in a faster manner.

These and other aspects, features, and advantages of the present disclosure are described in or are apparent from the following detailed description of the exemplary, non-limiting embodiments of the present disclosure and the accompanying figures. Other aspects and features of embodiments of the present disclosure will become apparent to those of ordinary skill in the art upon reviewing the following description of specific, exemplary embodiments of the present disclosure in concert with the figures.

While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the systems, methods, and/or apparatuses discussed herein. In similar fashion, while exemplary embodiments may be discussed below as device, system, or method embodiments, it is to be understood that such exemplary embodiments can be implemented in various devices, systems, and methods of the present disclosure.

Any benefits, advantages, or solutions to problems that are described herein with regard to specific embodiments are not intended to be construed as a critical, required, or essential feature(s) or element(s) of the present disclosure or the claims.

BRIEF DESCRIPTION OF THE SEVERAL VIEWS OF THE DRAWINGS

As required, detailed exemplary embodiments of the present disclosure are disclosed herein; however, it is to be understood that the disclosed embodiments are merely exemplary of the present disclosure that may be embodied in various and alternative forms, within the scope of the present disclosure. The figures are not necessarily to scale; some features may be exaggerated or minimized to illustrate details of particular components. Therefore, specific structural and functional details disclosed herein are not to be interpreted as limiting, but merely as a basis for the claims and as a representative basis for teaching one skilled in the art to employ the present disclosure.

The exemplary embodiments of the present disclosure will be described in detail, with reference to the following figures, wherein like reference numerals refer to like parts throughout the several views, and wherein.

DETAILED DESCRIPTION OF EXEMPLARY EMBODIMENTS OF THE PRESENT DISCLOSURE

Figure 1:
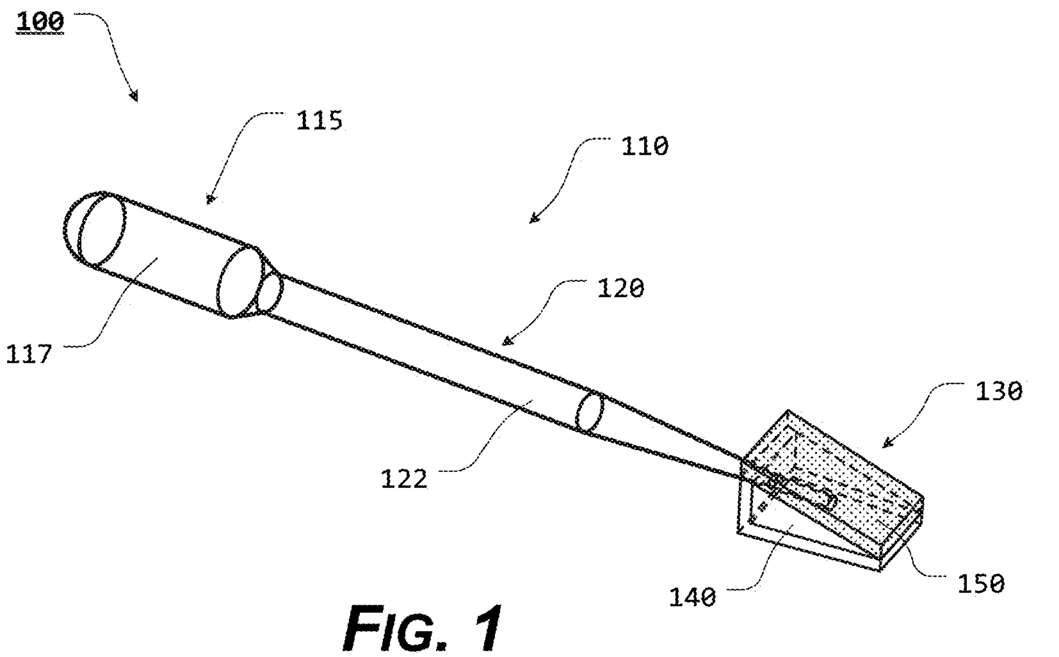
FIG. 1 illustrates a perspective view of certain exemplary components of an exemplary embodiment of a sponge assembly, according to the present disclosure.
Figure 2:
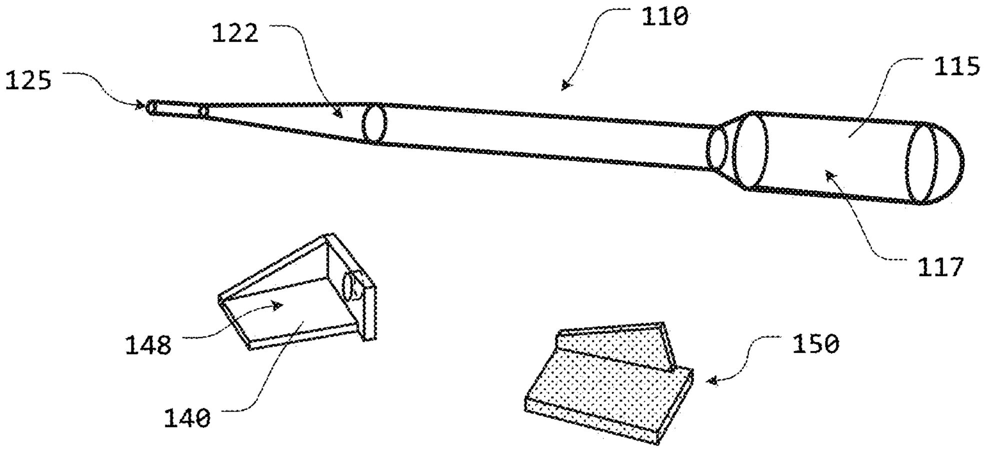
FIG. 2 illustrates a perspective view of certain exemplary components of an exemplary embodiment of a sponge assembly, according to the present disclosure.
Figure 3:
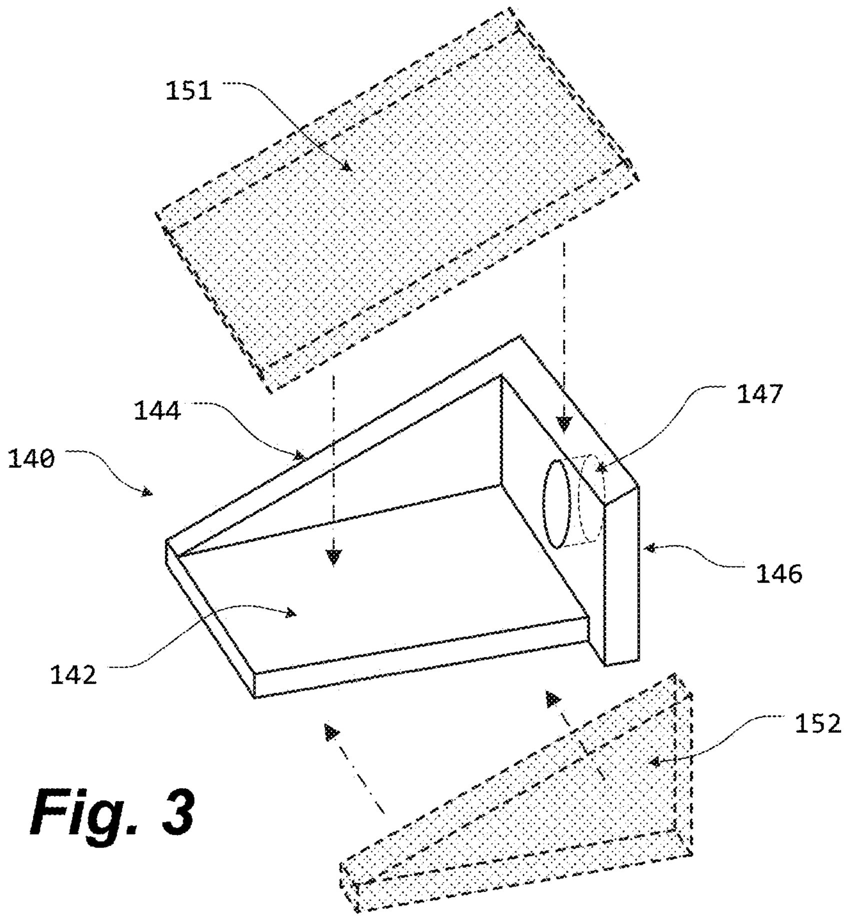
FIG. 3 illustrates an exploded a partially assembled, perspective view of certain exemplary components of an exemplary embodiment of a sponge element, according to an exemplary embodiment of the present disclosure.
Figure 4:
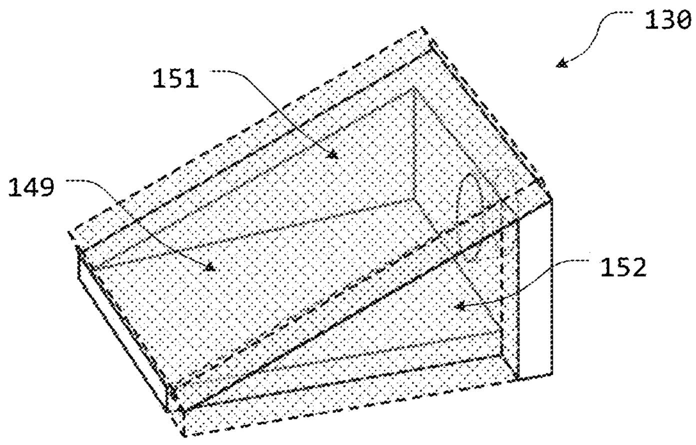
FIG. 4 illustrates an upper perspective view of certain exemplary components of an exemplary embodiment of a sponge element, according to an exemplary embodiment of the present disclosure.
Figure 5:
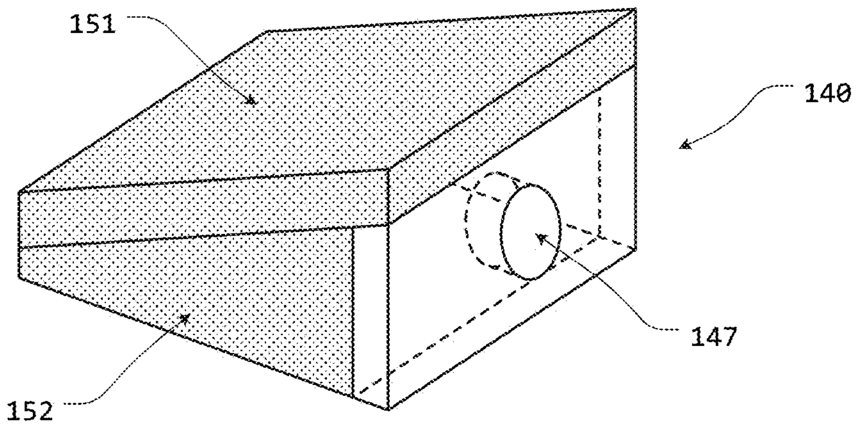
FIG. 5 illustrates a rear perspective view of certain exemplary components of an exemplary embodiment of a sponge element, according to an exemplary embodiment of the present disclosure.
Figure 6:
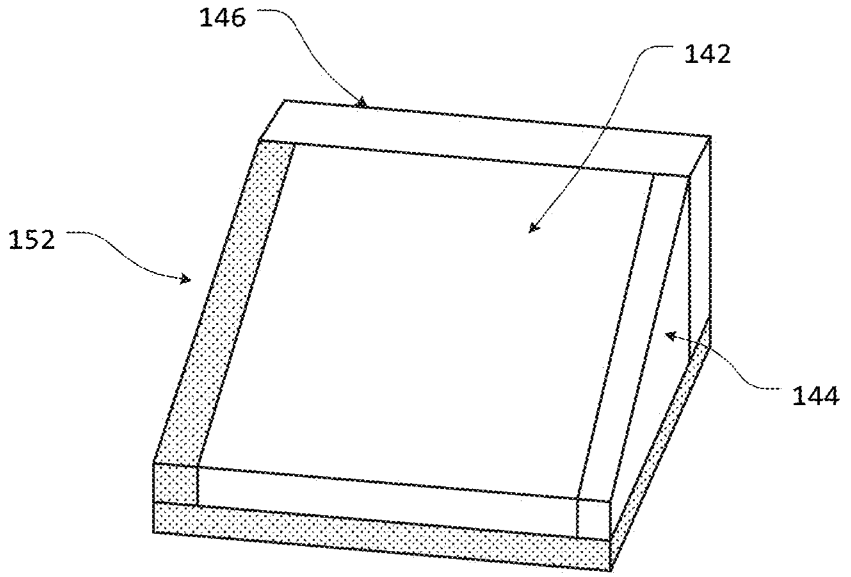
FIG. 6 illustrates a lower perspective view of certain exemplary components of an exemplary embodiment of a sponge element, according to an exemplary embodiment of the present disclosure.
Figure 7:
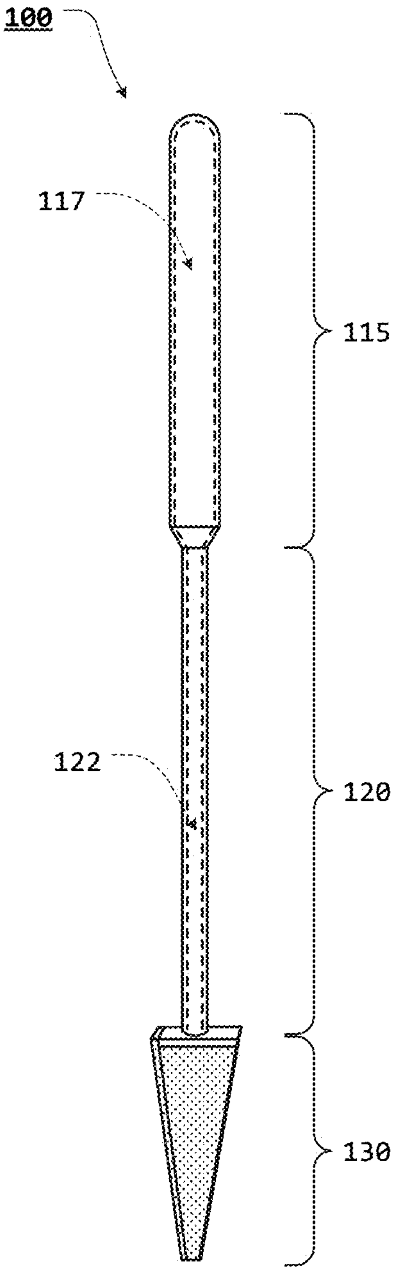
FIG. 7 illustrates a side view of certain exemplary components of an exemplary embodiment of a sponge assembly, according to the present disclosure.
Figure 8:
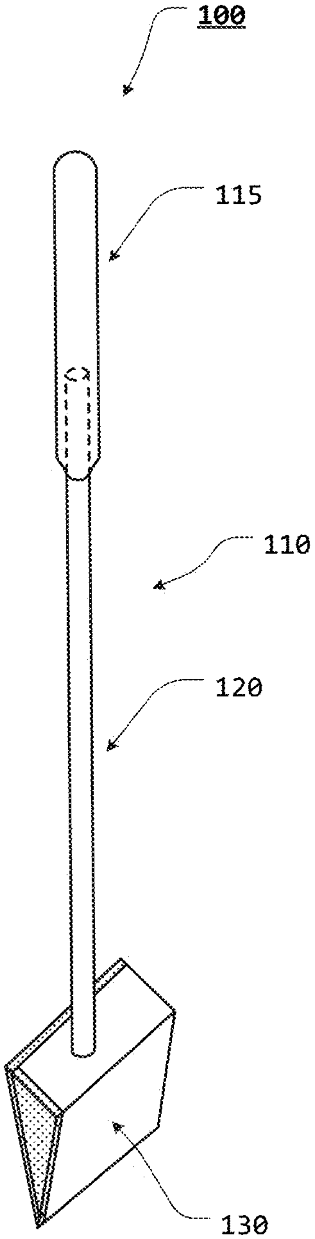
FIG. 8 illustrates an upper perspective view of certain exemplary components of an exemplary embodiment of a sponge assembly, according to the present disclosure.
Figure 9:
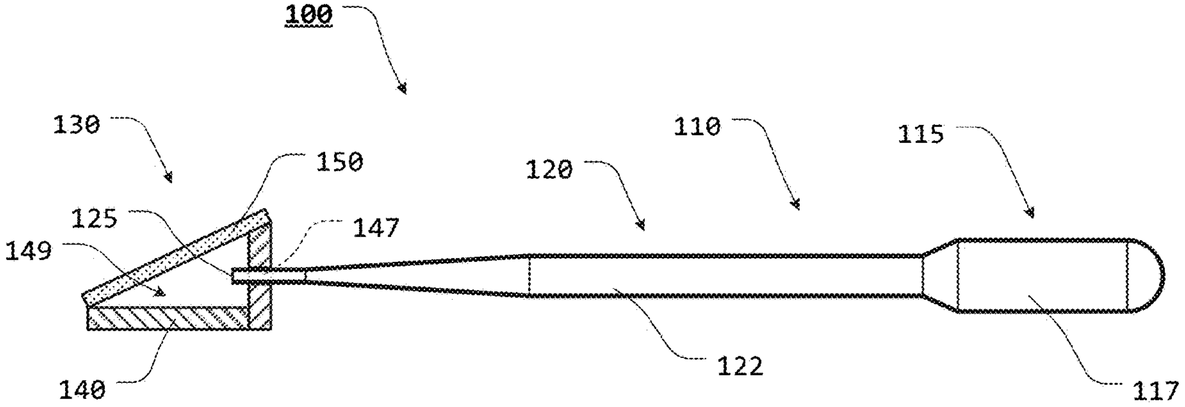
FIG. 9 illustrates a side, cross-sectional view of certain exemplary components of an exemplary embodiment of a sponge assembly, according to the present disclosure.

For simplicity and clarification, the design factors and operating principles of the sponge assembly according to the present disclosure are explained with reference to various exemplary embodiments of a sponge assembly according to the present disclosure. The basic explanation of the design factors and operating principles of the sponge assembly is applicable for the understanding, design, and operation of the sponge assembly of the present disclosure. It should be appreciated that the sponge assembly can be adapted to many applications where a surgical sponge or surgical sponge assembly can be used.

As used herein, the word “may” is meant to convey a permissive sense (i.e., meaning “having the potential to”), rather than a mandatory sense (i.e., meaning “must”). Unless stated otherwise, terms such as “first” and “second”, “right” and “left”, “top” and “bottom”, “upper” and “lower”, and “horizontal” and “vertical” are used to arbitrarily distinguish between the exemplary embodiments and/or elements such terms describe. Thus, these terms are not necessarily intended to indicate temporal or other prioritization of such exemplary embodiments and/or elements.

As used herein, and unless the context dictates otherwise, the term “coupled” is intended to include both direct coupling (in which two elements that are coupled to each other contact each other) and indirect coupling (in which at least one additional element is located between the two elements). The term coupled, as used herein, is defined as connected, although not necessarily directly, and not necessarily mechanically. The terms “a” and “an” are defined as one or more unless stated otherwise.

Throughout this application, the terms “comprise” (and any form of comprise, such as “comprises” and “comprising”), “have” (and any form of have, such as “has” and “having”), “include”, (and any form of include, such as “includes” and “including”) and “contain” (and any form of contain, such as “contains” and “containing”) are used as open-ended linking verbs. It will be understood that these terms are meant to imply the inclusion of a stated element, integer, step, or group of elements, integers, or steps, but not the exclusion of any other element, integer, step, or group of elements, integers, or steps. As a result, a system, method, or apparatus that “comprises”, “has”, “includes”, or “contains” one or more elements possesses those one or more elements but is not limited to possessing only those one or more elements. Similarly, a method or process that “comprises”, “has”, “includes” or “contains” one or more operations possesses those one or more operations but is not limited to possessing only those one or more operations.

It should also be appreciated that, for simplicity and clarification, certain embodiments of the present disclosure may be described using terms such as “front”, “back”, “rear”, “right”, “left”, “upper”, “lower”, “outer”, and/or “inner”. However, it should be understood that these terms are merely used to aid in understanding the present disclosure are not to be construed as limiting the systems, methods, devices, and/or apparatuses of the present disclosure. Additionally, it should be appreciated that, unless otherwise stated, the design factors and operating principles of the presently disclosed sponge assembly may optionally be used in a “mirror image” assembly, wherein elements shown and/or described as being included in or on a drive end portion may optionally be included in or on a non-drive end portion. Alternatively, certain of the elements that are shown and/or described as being included in or on a back portion may optionally be included in or on a front portion, or vice versa.

It should also be appreciated that the terms “sponge assembly”, “pipette”, “sponge element”, “sponge portion”, and “thrombin coating” are used for basic explanation and understanding of the operation of the systems, methods, and apparatuses of the present disclosure. Therefore, the terms “sponge assembly”, “pipette”, “sponge element”, “sponge portion”, and “thrombin coating” are not to be construed as limiting the systems, methods, and apparatuses of the present disclosure.

Furthermore, it should be appreciated that, for simplicity and clarification, the embodiments of the present disclosure will be shown and/or described with reference to a certain number of sides or surfaces of the sponge element being covered by various portions of one or more sponge portions. However, it should be appreciated that the inclusion and/or specific placement of any number of sponge portions is not essential to the sponge assembly of the present disclosure.

Turning now to the appended drawing figures, FIGS. 1-11 illustrate certain elements and/or aspects of an exemplary embodiment of a sponge assembly 100, according to the present disclosure. As illustrated, the sponge assembly 100 comprises at least some of a pipette 110 and sponge element 130.

In certain exemplary embodiments, as illustrated most clearly in FIGS. 3-6, the sponge element 130 includes at least some of a sponge support 140 and a sponge portion 150.

In various exemplary, nonlimiting embodiments, the sponge support 140 is a substantially triangularly shaped support, formed of one or more walls or wall portions. As illustrated, the sponge support 140 may optionally include a sponge support bottom wall 142, a sponge support side wall 144, and a sponge support rear wall 146. In these exemplary embodiments, the sponge support 140 forms a substantially right triangle, wherein the sponge support bottom wall 142 forms a base leg, the sponge support rear wall 146 forms a height leg, and an upper edge portion of the sponge support sidewall 144 forms a hypotenuse of the sponge support 140. In these exemplary embodiments, an approximately 90° angle is formed between planar surfaces of the sponge support bottom wall 142 and the sponge support rear wall 146.

In certain exemplary embodiments, one or more of the sponge support bottom wall 142, the sponge support side wall 144, and/or the sponge support rear wall 146 are individual wall elements attached or coupled to form the sponge support 140. Alternatively, the sponge support 140 may be formed from any number or combination of walls, including, for example, a single, continuous wall. Thus, it should be appreciated that the sponge support 140 may be formed of a single, continuous wall portion, two or more coupled or joined wall portions, or multiple coupled or joined wall portions.

In certain exemplary embodiments, the sponge support rear wall 146 extends substantially perpendicularly from a portion of the sponge support bottom wall 142. Similarly, the sponge support side wall 144 extends substantially perpendicularly from a portion of the sponge support bottom wall 142. In certain exemplary embodiments, terminal portions of the sponge support side wall 144 and the sponge support rear wall 146 are joined proximate a corner or edge portion of the sponge support bottom wall 142.

In various exemplary embodiments, the sponge support 140 is substantially rigid and is formed of a polymeric material such as a polymeric composite. Alternate materials of construction may include one or more of the following: steel, aluminum, titanium, and/or other metals, as well as various alloys and composites thereof, glass-hardened polymers, polymer or fiber reinforced metals, carbon fiber or glass fiber composites, continuous fibers in combination with thermoset and thermoplastic resins, chopped glass or carbon fibers used for injection molding compounds, laminate glass or carbon fiber, epoxy laminates, woven glass fiber laminates, impregnate fibers, polyester resins, epoxy resins, phenolic resins, polyimide resins, cyanate resins, high-strength plastics, nylon, glass, or polymer fiber reinforced plastics, thermoform and/or thermoset sheet materials, or the like, and/or various combinations of the foregoing.

Thus, it should be understood that the material or materials used to form the sponge support 140 and/or various components of the sponge support 140 is a design choice based on the desired appearance and functionality of the sponge support 140.

In certain exemplary embodiments, the sponge support 140 may comprise a single, continuous sponge support 140 or may comprise two or more sponge support 140 walls attached or coupled together. In certain exemplary embodiments, adjacent portions of the sponge support 140 may be attached or coupled together by one or more attachment elements comprising, for example, a chemical adhesive. Alternatively, the attachment elements may optionally comprise adhesive bonding, heat, ultrasonic, or other types of welding, screws, rivets, pins, mating hook and loop portions, snap or releasable fasteners, or other known or later developed means or methods for permanently or releasably attaching or coupling portions of the sponge support 140 to one another.

The sponge support bottom wall 142, the sponge support side wall 144, and the sponge support rear wall 146 defining at least portions of an at least partial cavity 148 within a portion of the sponge support 140.

A pipette aperture 147 is formed through a portion of the sponge support rear wall 146. The pipette aperture 147 is formed so as to allow fluid communication through the sponge support rear wall 146, between at least a portion of the at least partial cavity 148 of the sponge support 140 and an exterior of the sponge support 140.

At least one sponge portion 150 is attached or coupled to the sponge support 140. In various exemplary embodiments, the at least one sponge portion 150 is attached or coupled to the sponge support 140 to cover or overlie at least a portion of the at least partial cavity 148 of the sponge support 140. In this manner, the at least partial cavity 148 is further defined between various interior surfaces of the sponge support 140 and various interior surfaces of the sponge portion 150, to form a fully enclosed or bounded cavity 149.

In certain exemplary embodiments, as illustrated, the sponge portion 150 includes a first sponge portion 151 and a second sponge portion 152. In these exemplary embodiments, the second sponge portion 152 is attached or coupled to a portion of the sponge support bottom wall 142 and the sponge support rear wall 146. Once attached or coupled, the second sponge portion 152 forms a sponge wall, opposite of and a substantial mirror image of the sponge support side wall 144.

The first sponge portion 151 is attached or coupled atop a portion of the sponge support bottom wall 142, the sponge support side wall 144, the sponge support rear wall 146, and the second sponge portion 152. In this manner, the first sponge portion 151 is attached or coupled atop a portion of the sponge support bottom wall 142, along the relative hypotenuse of the sponge support 140.

When the sponge support bottom wall 142, the sponge support side wall 144, the sponge support rear wall 146, the first sponge portion 151, and the second sponge portion 152 are attached, coupled, or formed, the at least partial cavity 148 is further defined within a portion of the sponge support 140.

Figure 10:
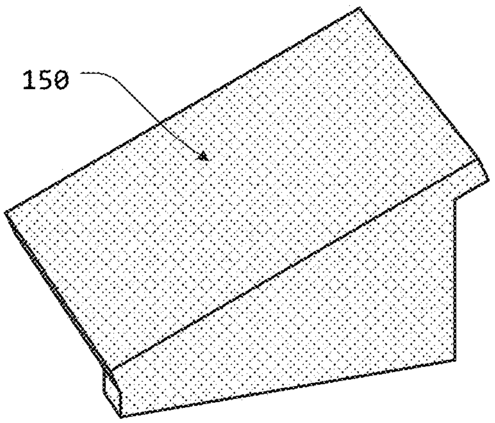
FIG. 10 illustrates an upper perspective view of an exemplary embodiment of a sponge portion, according to the present disclosure.
Figure 11:
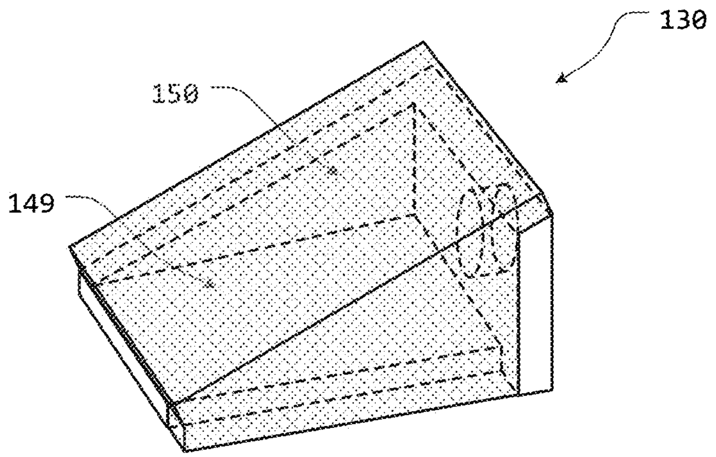
FIG. 11 illustrates an upper perspective view of certain exemplary components of an exemplary embodiment of a sponge element, according to the present disclosure.

In various exemplary embodiments, as illustrated in FIGS. 10 and 11, the sponge portion 150 comprises a single, unitary sponge portion 150 incorporating the first sponge portion 151 and the second sponge portion 152 into a single, unitary element.

In certain exemplary, nonlimiting embodiments, the sponge portion 150 comprises a highly absorbent cellulose material for fluid wicking and containment and are able to absorb and/or diffuse fluids. In certain exemplary embodiments, the sponge portion 150 comprise a porous, polyvinyl alcohol foam.

In certain exemplary, nonlimiting embodiments, a thrombin coating or hemostatic agent is applied to a portion of or at least partially impregnated into a portion of the sponge portion 150. If included the thrombin coating or hemostatic agent is a systemic drug that inhibits fibrinolysis or promotes coagulation. By including a thrombin coating or hemostatic agent on or in a portion of the sponge portion 150, the sponge element 130 allows for placement of locally acting hemostatic agents to cause vasoconstriction or promote platelet aggregation.

The pipette 110 includes a pipette bulb portion 115 having a hollow interior bulb portion 117 and an elongate pipette body portion 120 having a hollow interior body portion 122. The pipette 110 extends from the pipette bulb portion 115 to the pipette body portion 120. The pipette body portion 120 extends from the pipette bulb portion 115 to a pipette terminal end 125. The pipette terminal end 125 includes an aperture, which allows fluid communication between the open pipette terminal end 125, the hollow interior body portion 122, and the hollow interior bulb portion 117.

In various exemplary embodiments, at least a portion of the pipette bulb portion 115 is formed of a substantially flexible, deformable material. In this manner, during use, at least a portion of the pipette bulb portion 115 can be pressed or squeezed to urge fluid from the hollow interior bulb portion 117, through the hollow interior body portion 122, and through the open pipette terminal end 125. When at least a portion of the pipette bulb portion 115 is released, an at least partial vacuum is created within the hollow interior bulb portion 117, allowing fluid to be drawn through the open pipette terminal end 125 and into at least a portion of the hollow interior body portion 122 and potentially into at least a portion of the hollow interior bulb portion 117.

In various exemplary embodiments, the pipette 110 may comprise a microcapillary pipette 110, which allows a measure of fluid to be drawn into at least a portion of the hollow interior body portion 122 through capillary action.

In various exemplary embodiments, a portion of a thrombin fluid or hemostatic agent may be supplied within the hollow interior bulb portion 117 or the hollow interior body portion 122 to be administered into the at least partial cavity 148 of the sponge element 130 and into the sponge portion 150 if the pipette bulb portion 115 is pressed or squeezed to urge the thrombin fluid or hemostatic agent from the pipette 110.

A portion of the pipette 110, proximate the pipette terminal end 125, is positioned adjacent or through the pipette aperture 147, such that the open pipette terminal end 125 is in fluid communication with the cavity 149 of the sponge support 140, via the pipette aperture 147.

Thus, by pressing or squeezing a portion of the pipette bulb portion 115 fluid can be urged from the hollow interior bulb portion 117 and/or through the hollow interior body portion 122, through the hollow interior body portion 122, through the open pipette terminal end 125, and into the cavity 149 of the sponge element 130. Alternatively, if at least a portion of the pipette bulb portion 115 is released from the pressed or squeezed position, an at least partial vacuum is created within the hollow interior bulb portion 117, allowing fluid to be drawn from the cavity 149 of the sponge element 130, through the open pipette terminal end 125 and into at least a portion of the hollow interior body portion 122 and potentially the hollow interior bulb portion 117.

In various exemplary embodiments, adjacent portions of the pipette 110 in the sponge element 130 are attached or coupled together by one or more attachment elements comprising, for example, a chemical adhesive. Alternatively, the attachment elements may optionally comprise adhesive bonding, heat, ultrasonic, or other types of welding, or other known or later developed means or methods for permanently or releasably attaching or coupling portions of the sponge support 140 to one another.

Alternatively, portions of the pipette 110 and the sponge support 140 may be formed as a single, integral unit. Thus, it should be appreciated that certain elements of the sponge assembly 100 may be formed as an integral unit. Alternatively, suitable materials can be used and sections or elements made independently and attached or coupled together, such as by adhesives, welding, screws, rivets, pins, or other fasteners, to form the various elements of the sponge assembly 100.

In various exemplary, nonlimiting embodiments, the pipette bulb portion 115 is approximately 3.0 cm in length, 0.5 cm in width, and has a 0.2 cm internal diameter. The pipette body portion 120 may optionally have a length of approximately 6.0 cm. The pipette body portion 120 may be formed as an integral portion of the pipette bulb portion 115 or may comprise a separate portion of material that extends approximately 1.0 cm inside the pipette bulb portion 115. The sponge support rear wall 146 (with or without the first sponge portion 151) may optionally be approximately 0.75 cm tall and approximately 1.50 cm wide. The length of the sponge support 140 (with or without the first sponge portion 151) may optionally be approximately 1.5 cm. Thus, the sponge assembly 100 may optionally have a total length of approximately 10.0 cm.

Notwithstanding the foregoing, it should also be understood that the overall size and shape of the sponge assembly 100 and the various portions thereof is a design choice based upon the desired functionality and/or appearance of the sponge assembly 100.

In various exemplary embodiments, the pipette bulb portion 115 may be supplemented by or replaced by a vacuum source.

During use, the sponge assembly 100 can be used to apply fluid to or aspirate fluid from a surgical area. For example, blood can obscure an ophthalmic surgeon's field of view during surgery, compromising the surgeon's ability to perform a procedure in a time-sensitive, safe manner. Current methods of clearing blood from the field are limited to the use of cellulose eye spears to absorb blood from the field. The sponge assembly 100 of the present disclosure allows for eye fluid clearing through the microcapillary pipette 110, applied hemostatic agents, and potentially increased dimensions.

During use, manipulation of the pipette bulb portion 115 can allow fluid to be urged into the sponge portion 150. Alternatively, manipulation of the pipette bulb portion 115 can allow fluid to be withdrawn or extracted from the sponge portion 150.

Thus, for example, if the sponge portion 150 becomes saturated with fluid, manipulation of the pipette bulb portion 115 can allow fluid to be extracted from the sponge portion 150, allowing additional fluid to be absorbed by the sponge portion 150. Alternatively, fluid within the hollow interior body portion 122 or the hollow interior bulb portion 117 may be urged, via manipulation of the pipette bulb portion 115, into the cavity 149 of the sponge support 140 to at least partially saturate the sponge portion 150.

A more detailed explanation of the instructions regarding how to utilize the sponge assembly 100 is not provided herein because it is believed that the level of description provided herein is sufficient to enable one of ordinary skill in the art to understand and practice the systems, methods, and apparatuses, as described.

While the present disclosure has been described in conjunction with the exemplary embodiments outlined above, the foregoing description of exemplary embodiments of the present disclosure, as set forth above, are intended to be illustrative, not limiting and the fundamental disclosed systems, methods, and/or apparatuses should not be considered to be necessarily so constrained. It is evident that the present disclosure is not limited to the particular variation set forth and many alternatives, adaptations modifications, and/or variations will be apparent to those skilled in the art.

Furthermore, where a range of values is provided, it is understood that every intervening value, between the upper and lower limit of that range and any other stated or intervening value in that stated range is encompassed within the present disclosure. The upper and lower limits of these smaller ranges may independently be included in the smaller ranges and is also encompassed within the present disclosure, subject to any specifically excluded limit in the stated range. Where the stated range includes one or both of the limits, ranges excluding either or both of those included limits are also included in the present disclosure.

It is to be understood that the phraseology of terminology employed herein is for the purpose of description and not of limitation. Unless defined otherwise, all technical and scientific terms used herein have the same meaning as commonly understood by one of ordinary skill in the art to which the present disclosure belongs.

In addition, it is contemplated that any optional feature of the inventive variations described herein may be set forth and claimed independently, or in combination with any one or more of the features described herein.

Accordingly, the foregoing description of exemplary embodiments will reveal the general nature of the present disclosure, such that others may, by applying current knowledge, change, vary, modify, and/or adapt these exemplary, non-limiting embodiments for various applications without departing from the spirit and scope of the present disclosure and elements or methods similar or equivalent to those described herein can be used in practicing the present disclosure. Any and all such changes, variations, modifications, and/or adaptations should and are intended to be comprehended within the meaning and range of equivalents of the disclosed exemplary embodiments and may be substituted without departing from the true spirit and scope of the present disclosure.

Also, it is noted that as used herein and in the appended claims, the singular forms "a", "and", "said", and "the" include plural referents unless the context clearly dictates otherwise. Conversely, it is contemplated that the claims may be so-drafted to require singular elements or exclude any optional element indicated to be so here in the text or drawings. This statement is intended to serve as antecedent basis for use of such exclusive terminology as "solely", "only", and the like in connection with the recitation of claim elements or the use of a "negative" claim limitation(s).

What is claimed is:

1. A sponge assembly, comprising:

a pipette wherein said pipette includes a pipette bulb portion having a hollow interior bulb portion and an elongate pipette body portion having a hollow interior body portion, wherein said pipette extends from said pipette bulb portion to said pipette body portion, wherein said pipette body portion extends from said pipette bulb portion to a pipette terminal end, and wherein said pipette terminal end includes an aperture, which allows fluid communication between said open pipette terminal end, said hollow interior body portion, and said hollow interior bulb portion;

a sponge support defining an at least partial cavity, wherein a pipette aperture is formed through a portion of said sponge support, and wherein at least a portion of said open pipette terminal end is in fluid communication with said pipette aperture, such that said open pipette terminal end is in fluid communication with said sponge support cavity, via said pipette aperture; and at least one sponge portion, wherein said at least one sponge portion is attached or coupled to said sponge support to cover at least a portion of said at least partial cavity.

2. The sponge assembly of claim 1, wherein said pipette comprises a microcapillary pipette.

3. The sponge assembly of claim 1, wherein a thrombin fluid or hemostatic agent is supplied within said hollow interior bulb portion or said hollow interior body portion.

4. The sponge assembly of claim 1, wherein said at least one sponge portion is at least partially impregnated with a thrombin fluid or hemostatic agent.

5. The sponge assembly of claim 1, wherein said pipette and said sponge support are formed as a single, integral unit.

6. The sponge assembly of claim 1, wherein said sponge support is substantially triangularly shaped.

7. The sponge assembly of claim 1, wherein said sponge support is formed of one or more walls.

8. The sponge assembly of claim 1, wherein said sponge support includes a sponge support bottom wall, a sponge support side wall, and a sponge support rear wall.

9. The sponge assembly of claim 1, wherein said at least one sponge portion comprises a first sponge portion and a second sponge portion.

10. A sponge assembly, comprising:

a pipette having a pipette bulb portion including a hollow interior bulb portion and an elongate pipette body portion including a hollow interior body portion, wherein said pipette extends from said pipette bulb portion to said pipette body portion, wherein said pipette body portion extends from said pipette bulb portion to an open terminal end having an aperture, wherein said aperture of said pipette terminal end allows fluid communication between said open pipette terminal end, said hollow interior body portion, and said hollow interior bulb portion;

a sponge support defining an at least partial cavity, wherein a pipette aperture is formed through a portion of said sponge support, and wherein at least a portion of said open pipette terminal end is in fluid communication with said pipette aperture, such that said open pipette terminal end is in fluid communication with said sponge support cavity, via said pipette aperture; and at least one sponge portion, wherein said at least one sponge portion is attached or coupled to said sponge support to cover at least a portion of said at least partial cavity.

11. The sponge assembly of claim 10, wherein a thrombin fluid or hemostatic agent is supplied within said hollow interior bulb portion or said hollow interior body portion.

12. The sponge assembly of claim 10, wherein said at least one sponge portion is at least partially impregnated with a thrombin fluid or hemostatic agent.

13. A sponge assembly, comprising:

a pipette having a pipette bulb portion and an elongate pipette body portion, wherein said pipette body portion extends from said pipette bulb portion to a pipette terminal end, and wherein said pipette terminal end includes an aperture, which allows fluid communication between said open pipette terminal end, a hollow interior body portion of said elongate pipette body portion, and a hollow interior bulb portion of said pipette bulb portion;

a sponge support defining an at least partial cavity, wherein a pipette aperture is formed through a portion of said sponge support, and wherein at least a portion of said open pipette terminal end is in fluid communication with said pipette aperture, such that said open pipette terminal end is in fluid communication with said sponge support cavity, via said pipette aperture; and at least one sponge portion, wherein said at least one sponge portion is attached or coupled to said sponge support to cover at least a portion of said at least partial cavity.

14. The sponge assembly of claim 13, wherein a thrombin fluid or hemostatic agent is supplied within said hollow interior bulb portion of said pipette bulb portion or said hollow interior body portion of said elongate pipette body portion.

15. The sponge assembly of claim 13, wherein said at least one sponge portion is at least partially impregnated with a thrombin fluid or hemostatic agent.

16. The sponge assembly of claim 13, wherein said pipette and said sponge support are formed as a single, integral unit.

17. The sponge assembly of claim 13, wherein said sponge support forms a substantially right triangle, wherein said sponge support bottom wall forms a base leg, said sponge support rear wall forms a height leg, and said upper edge portion of said sponge support sidewall forms a hypotenuse of said sponge support.

18. The sponge assembly of claim 13, wherein said sponge support is formed of one or more walls.

19. The sponge assembly of claim 13, wherein said sponge support includes a sponge support bottom wall, a sponge support side wall, and a sponge support rear wall.

20. The sponge assembly of claim 13, wherein said at least one sponge portion comprises a first sponge portion and a second sponge portion.

* * * * *